(12) United States Patent
Creed et al.

(10) Patent No.: US 7,763,865 B2
(45) Date of Patent: Jul. 27, 2010

(54) RADIOTHERAPEUTIC APPARATUS

(75) Inventors: Quentin Creed, Brighton (GB); Duncan Neil Bourne, Redhill (GB); Ralph Peter Streamer, Horsham (GB)

(73) Assignee: Elekta AB, Stockholm (SE)

( * ) Notice: Subject to any disclaimer, the term of this patent is extended or adjusted under 35 U.S.C. 154(b) by 559 days.

(21) Appl. No.: 11/662,459

(22) PCT Filed: Sep. 29, 2005

(86) PCT No.: PCT/GB2005/003743

§ 371 (c)(1), (2), (4) Date: Mar. 9, 2007

(87) PCT Pub. No.: WO2006/035232

PCT Pub. Date: Apr. 6, 2006

(65) Prior Publication Data

US 2007/0262274 A1    Nov. 15, 2007

(30) Foreign Application Priority Data

Sep. 30, 2004   (GB) ................. 0421713.9

(51) Int. Cl.
  *G01J 1/00*  (2006.01)
  *G01N 21/00*  (2006.01)
  *G01N 23/00*  (2006.01)
  *G02B 5/00*  (2006.01)
  *G21K 1/00*  (2006.01)

(52) U.S. Cl. ................. 250/491.1; 250/505.1

(58) Field of Classification Search ........... 250/505.1, 250/491.1; 359/566–569, 571, 529–530; 600/1, 247; 378/65, 152, 20; 607/88–95

See application file for complete search history.

(56) References Cited

U.S. PATENT DOCUMENTS

| 4,157,475 | A |   | 6/1979  | Stock et al. |
| 4,343,997 | A |   | 8/1982  | Heinz et al. ................. 250/505 |
| 4,794,629 | A | * | 12/1988 | Pastyr et al. ................ 378/152 |
| 4,989,964 | A | * | 2/1991  | Meise ........................ 359/851 |
| 5,004,673 | A | * | 4/1991  | Vlannes ...................... 359/571 |
| 5,039,867 | A | * | 8/1991  | Nishihara et al. ......... 250/491.1 |
| 5,748,703 | A | * | 5/1998  | Cosman ...................... 378/152 |
| 5,818,902 | A | * | 10/1998 | Yu .............................. 378/65 |
| 6,001,054 | A | * | 12/1999 | Regulla et al. ................. 600/1 |

(Continued)

FOREIGN PATENT DOCUMENTS

WO    WO 01/78579    10/2001

*Primary Examiner*—Jack I Berman
*Assistant Examiner*—Brooke Purinton
(74) *Attorney, Agent, or Firm*—Z. Peter Sawicki; Westman, Champlin & Kelly, P.A.

(57) ABSTRACT

The present invention therefore provides a method of treating the surface of an item for a radiotherapy apparatus, comprising the steps of machining into a planar reflective surface of the item a stepped profile, each step having a first surface angled to the planar reflective surface such that, in use, the first surface reflects light incident on the planar reflective surface away from the isocenter of the radiotherapy apparatus and a second surface angled with respect to the planar reflective surface and the first surface such that, in use, the second surface is shadowed from light incident on the planar reflective surface by the first surface, the steps having a depth which does not exceed 2.15% of the total depth of the item.

17 Claims, 3 Drawing Sheets

U.S. PATENT DOCUMENTS

| | | | |
|---|---|---|---|
| 6,048,474 A * | 4/2000 | Storr et al. | 219/69.14 |
| 6,167,114 A * | 12/2000 | Siochi | 378/65 |
| 6,233,096 B1 * | 5/2001 | Marcelli et al. | 359/574 |
| 6,469,827 B1 * | 10/2002 | Sweatt et al. | 359/351 |
| 6,471,630 B1 * | 10/2002 | Sioshansi et al. | 600/1 |
| 6,624,431 B1 | 9/2003 | Foster et al. | 250/505.1 |
| 6,639,235 B1 * | 10/2003 | Gurgoze | 250/505.1 |
| 6,714,627 B1 * | 3/2004 | Brown et al. | 378/152 |
| 6,825,988 B2 * | 11/2004 | Bristol | 359/634 |
| 6,930,834 B2 * | 8/2005 | Ogusu et al. | 359/571 |
| 7,015,490 B2 * | 3/2006 | Wang et al. | 250/505.1 |
| 7,083,610 B1 * | 8/2006 | Murray et al. | 607/88 |
| 7,095,823 B2 * | 8/2006 | Topolnjak et al. | 378/152 |
| 7,108,423 B2 * | 9/2006 | Schmitt | 378/206 |
| 7,154,107 B2 * | 12/2006 | Yanagisawa et al. | 250/492.3 |
| 7,167,542 B2 * | 1/2007 | Juschka et al. | 378/152 |
| 7,247,873 B2 * | 7/2007 | Arakawa | 250/583 |
| 7,257,196 B2 * | 8/2007 | Brown et al. | 378/150 |
| 7,397,901 B1 * | 7/2008 | Johnsen | 378/147 |
| 7,397,902 B2 * | 7/2008 | Seeber et al. | 250/505.1 |
| 2001/0036017 A1 | 11/2001 | Brown et al. | 359/641 |
| 2002/0101959 A1 | 8/2002 | Kato et al. | 378/152 |
| 2004/0100699 A1 * | 5/2004 | Cowan et al. | 359/599 |
| 2004/0156478 A1 * | 8/2004 | Appleby et al. | 250/505.1 |
| 2005/0180013 A1 * | 8/2005 | Heidemann et al. | 359/566 |

* cited by examiner

Fig 2a - PRIOR ART

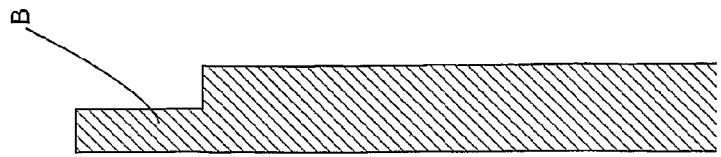
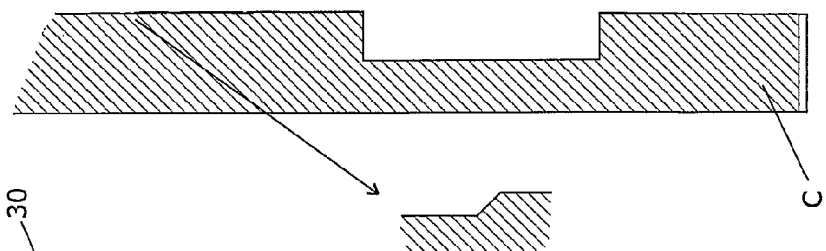
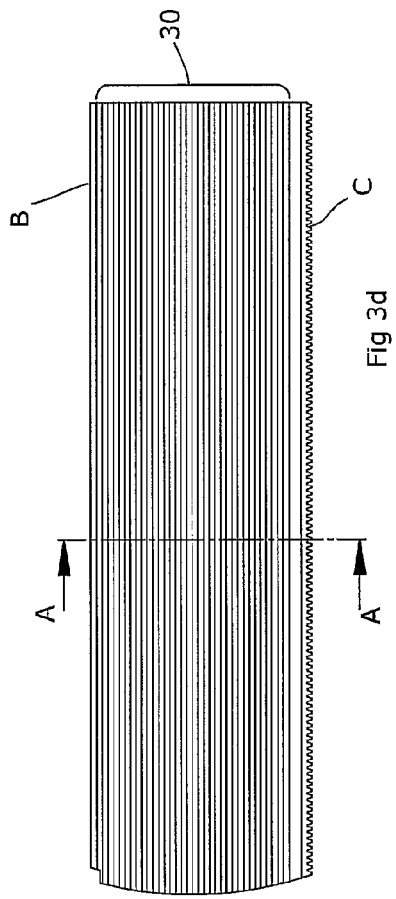
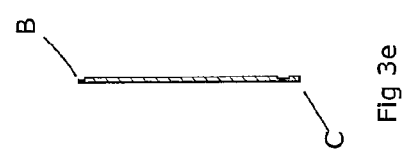
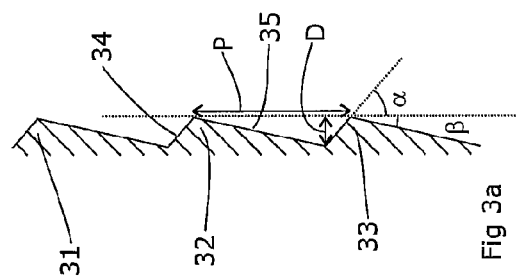

US 7,763,865 B2

RADIOTHERAPEUTIC APPARATUS

CROSS-REFERENCE TO RELATED APPLICATION

This Application is a Section 371 National Stage Application of International Application No. PCT/GB2005/003743, filed 29 Sep. 2005 and published as WO 2006/035232 on 06 Apr. 2006, in English.

1. Field of the Invention

The present invention relates to radiotherapeutic apparatus.

2. Background Art

The use of radiation in various forms to treat cancers and the like is an established art. A beam of harmful radiation is directed towards a patient and is absorbed by the tumourous cells, causing their death. One of the problems inherent in doing so is that the radiation is likewise capable of causing harm to healthy tissue around the tumour.

In practice, a number of measures are taken to limit the irradiation of non-tumourous tissue. An important measure is the use of suitable collimators, including so-called "multi-leaf collimators" or MLCs. These include a number of leaves arranged adjacently so that they can project into the beam. Each leaf is independently adjustable and thus the tips of the leaves can define an arbitrarily shaped aperture corresponding to the shape of the tumour. An example of an MLC is shown at EP-A-0,314,214, the disclosure of which is hereby incorporated by reference.

This aperture, or the aperture of an alternative collimator, will of course need to be aligned to the precise position of the patient. This can be done in a number of ways, but a common first step is to project visible light along the beam path so that a bright image is visible on the patient showing the outline of the collimator. This provides a good first check of the patient position.

A problem commonly encountered in this step is that the light can reflect off internal surfaces in the radiation source. Where an MLC is used, this includes the sides of the leaves themselves. This can produce "ghost" images, that is bright areas in the image that are simply the result of internal reflections and do not correspond to irradiated areas. With a complex MLC shape in particular, these reflections can be distracting.

SUMMARY OF THE INVENTION

The present invention therefore provides a method of treating the surface of an item for a radiotherapy apparatus, comprising the steps of machining into a planar reflective surface of the item a stepped profile, each step having a first surface angled to the planar reflective surface such that, in use, the first surface reflects light incident on the planar reflective surface away from the isocentre of the radiotherapy apparatus and a second surface angled with respect to the planar reflective surface and the first surface such that, in use, the second surface is shadowed from light incident on the planar reflective surface by the first surface, the steps having a depth which does not exceed 2.15% of the total depth of the item.

Typically, for an MLC leaf installed in a radiotherapeutic apparatus, light will be incident on the planar surface at an angle of about 0.6°, in this case, the first surface may conveniently be provided at an angle of between about 10° and 90°. More desirably, the first surface is provided at an angle of between about 30° and 60°, most conveniently, the first surface is provided at an angle of about 45°.

The depth and pitch of the steps and angle of the second surface are selected with respect to the first surface such that the second surface is entirely shadowed by the first surface when light is incident on the first surface. The relationship can be defined as in FIG. 4 hereto.

FIG. 4 shows (schematically) a section through a step of a stepped profile provided in accordance with the invention. The step has a depth z and a pitch (x+y). The step has first and second surfaces D and C which are inclined to the planar surface of the item shown in dotted outline. Light is incident on the planar surface at an angle s. The angles of surfaces D and C respectively to the planar surface are (90°−A) and B.

To minimise undesirable reflections, it is desired that surface D shade surface C from light incident on the planar surface at angle s. This can be achieved by B being greater than or equal to s, A being less than or equal to (s+45°) and greater than or equal to s.

The pitch of the steps is desirably of the order of about 0.9 to 2.5 mm, preferably about 2 mm, the depth of the steps is desirably of the order of 0.015 mm to 0.03 mm, preferably about 0.02 mm.

The steps may be provided across substantially all or just a portion of the planar surface. Desirably, the steps are substantially identical in geometry and are equally spaced across the stepped profile.

Various commonplace machining methods may be used to machine the steps, for example, but not strictly limited to; milling, wire eroding, spark eroding or EDM.

Once the machining has been completed, the item can then be assembled with other items to form a radiotherapeutic apparatus. Typically, the item is a leaf of a multi-leaf collimator since these display the worst reflections, but other internal surfaces of the apparatus will also benefit.

The present invention also relates to the corresponding products, that is items which, in use, have a surface exposed to the interior passageway of a radiotherapy apparatus, at least part of that surface having been subjected to the method of treating a surface hereinbefore described.

BRIEF DESCRIPTION OF THE DRAWINGS

An embodiment of the present invention will now be described by way of example, with reference to the accompanying figures in which;

FIG. 3 shows the surface treatment method of the present invention; and

DETAILED DESCRIPTION OF THE EMBODIMENTS

Figure 1:
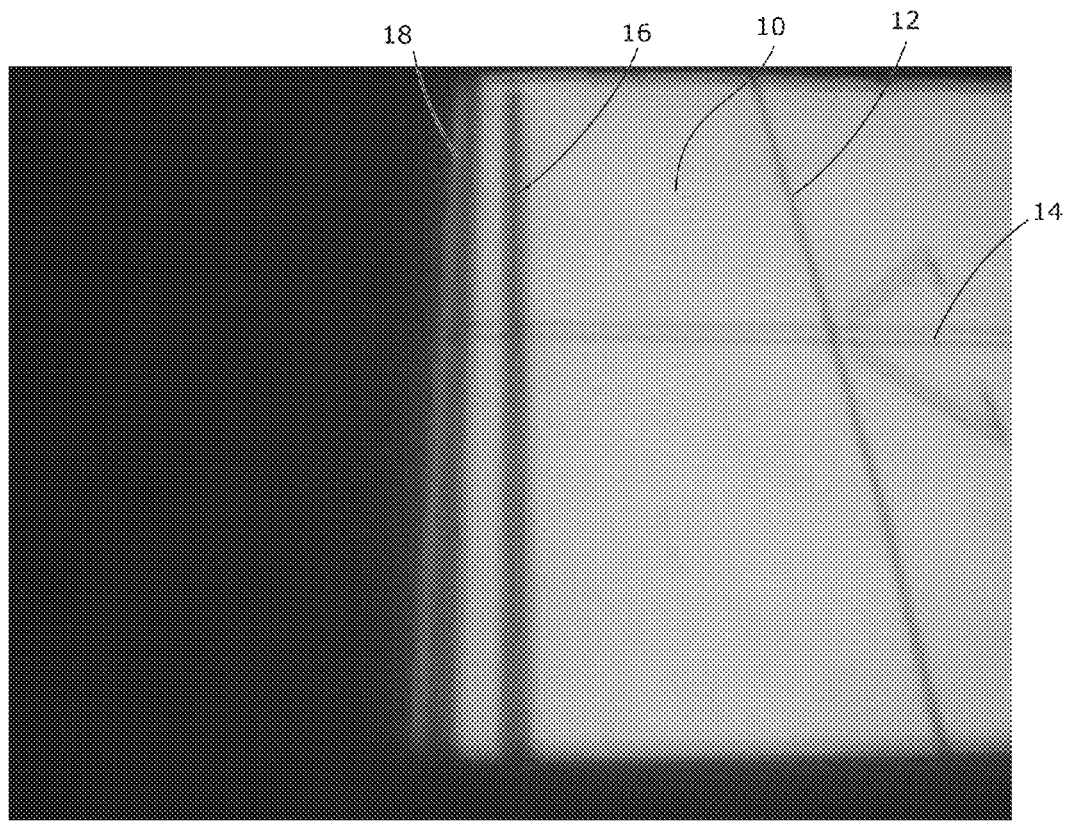
FIG. 1 shows a known MLC arrangement and an undesired reflection therefrom.

FIG. 1 shows a typical example of an illuminated treatment field. A bright area 10 is visible which will eventually be irradiated. Cross hairs 12, 14 can be seen which highlight the centre of the field to assist in positioning the patient. The extent of the field 10 is defined by a multi-leaf collimator, which in this case is providing a field which is otherwise square apart from a single leaf 16 which extends into the square field. A reflected image 18 can be seen outside the correct extent of the field 10, which is caused by light reflecting from one face of the leaf 16 and falling outside the treatment area 10.

These reflections arise through the very flat surface presented by various items within the beam path, such as the MLC leaves. However, particularly in the case of the MLC leaves, these surfaces must have a high flatness tolerance of the order of less than 30 microns in order to fulfill their functions during irradiation. Specifically, the purpose of the MLC leaves is to block the passage of radiation, and where several leaves are arranged adjacent to each other there will ideally be a complete block without any radiation leaking between leaves. As a result, large scale roughness to the surface is not acceptable.

Attempts have been made to reduce reflections by applying various coatings or paints to the reflecting surfaces of the apparatus. Various forms of coatings suffer from the problem that the gap between MLC leaves is usually designed at 90 microns and that therefore the coating must not be greater than 40 microns or else the leaves will jam. Matt paints produce a surface that is visually non-reflective when viewed perpendicularly, but that the very small angles at which the light is incident on an MLC leaf the paint is still highly reflective. Furthermore, the paint surface is rarely flat and this causes quality control problems. Of course, any paint layer must add thickness to the leaves, and where there is close contact between surfaces the paint can be eroded due to wear.

Dissimilar material coatings could be applied, but suffer from the risk of de-lamination and are unlikely to be flat in the context of a 40 micron layer.

One possibility is to oxidise the surface of the leaf, and this proves to be beneficial in that a significant reduction in the reflectivity is obtained. However, if the oxidation is limited to levels that do not adversely affect the physical properties of the leaf, the reduction in reflectivity is inadequate.

It will thus be appreciated that, in order to allow continued reliable operation of a multi leaf collimator whose leaves are treated in this way, the method must not significantly distort the geometrical characteristics of the surface to which it is applied, in particular its flatness.

Figure 2B:
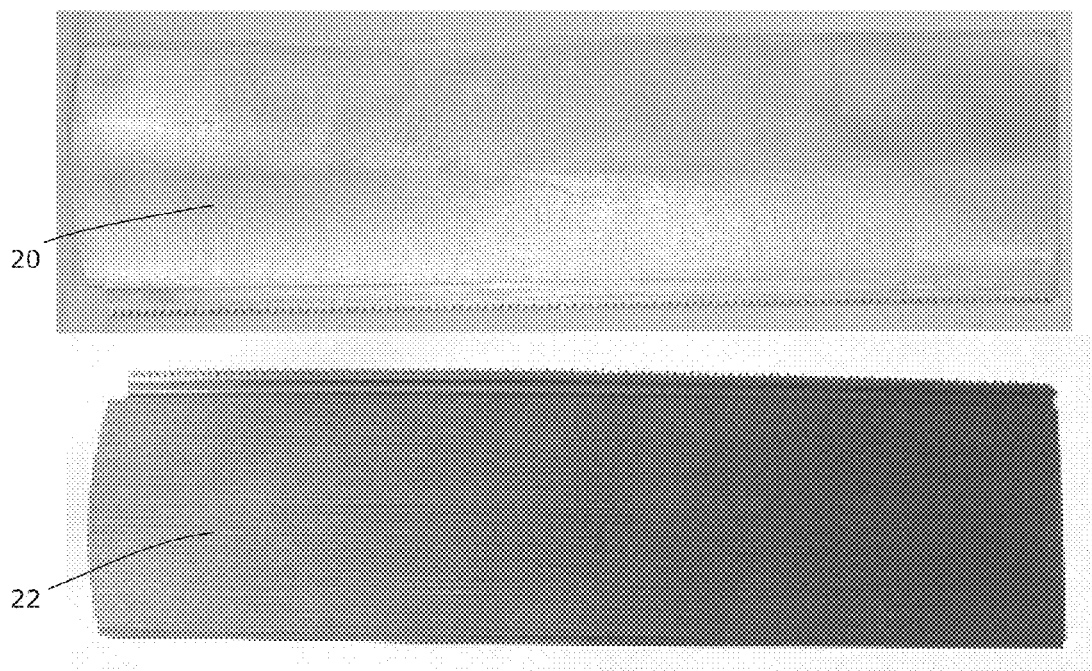
FIG. 2 shows a known MLC leaf and a leaf treated according to the present invention.
Figure 4:
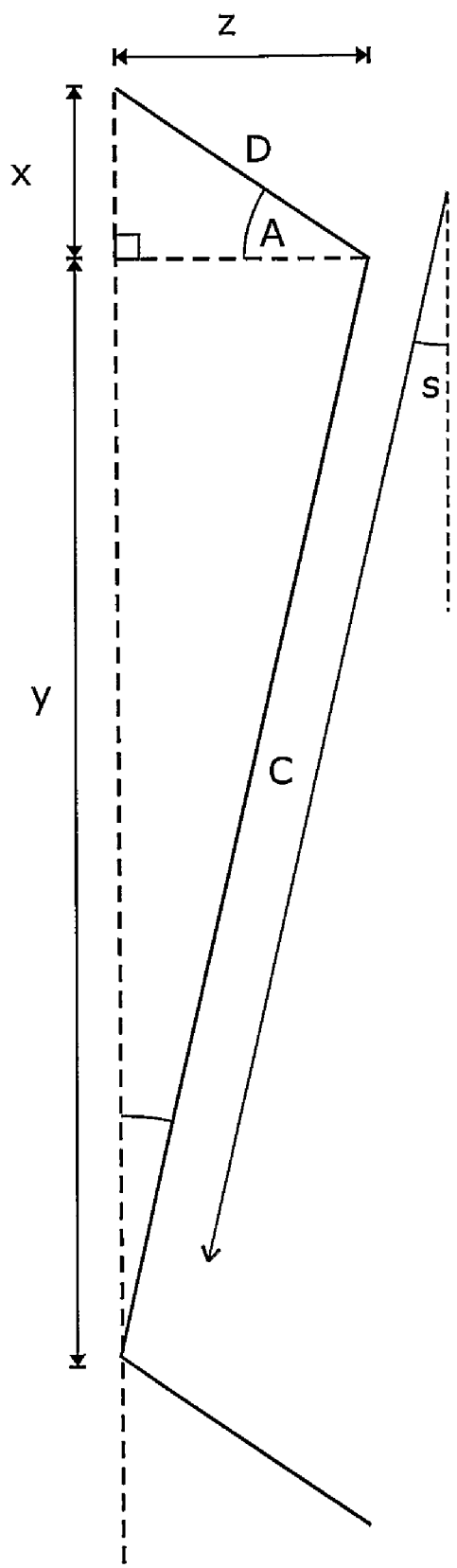
FIG. 4 illustrates the angle of the steps.

FIG. 2 shows a prior art plate 20 and a plate 22 into which a stepped profile has been machined in accordance with the invention. As can be seen, the upper and lower edges of the plate 22 have been left unmachined so that the plate does not interfere with the normal operation of the leaf, which is usually held in position at these unmachined edges.

FIG. 3 shows in more detail and in various views, an embodiment of an MLC leaf to which the machining method has been applied. FIG. 3(d) shows a plan view of the planar surface of the leaf to which the machining method has been applied. FIG. 3(e) shows to scale a section of the leaf viewed along line A-A on FIG. 3(d). FIG. 3(a) shows in larger scale a portion of the section shown in FIG. 3(e) illustrating the profile of the steps machined into the planar surface. FIGS. 3(b) and 3(c) respectively show in larger scale edges of the leaf identified by reference numerals B and C in FIG. 3(e).

As can be seen from FIG. 3, the collimator leaf has two edges B, C by which it can be secured in an MLC apparatus. Extending between the two edges is a stepped profile 30 comprising a plurality of geometrically identical and equally spaced steps 31, 32, 33 . . . . Each step has a first surface 34 which, when the MLC is in use, reflects light incident on the planar surface away from the isocentre of the apparatus, and a second surface 35. The first surface is angled to the planar surface at an angle a which in the embodiment shown is 45°. The second surface is angled to the planar surface at an angle $\beta$ which in the embodiment shown is ~0.6°. Each step has a depth D and a pitch P. In the embodiment shown, D and P are respectively about 0.02 mm and 1.92 mm. Each step extends the full length of the leaf.

It is to be understood that the stepped profile illustrated in FIG. 3 is purely exemplary.

In practice, whilst the reflectivity of a surface is difficult to define or measure, there are accepted forms of measurement apparatus which produce an output in Lux. Whilst the specific number will often be particular to the measurement apparatus used, these results are comparable across different surfaces. Table 1 below shows the reflectivity of various forms of surface treatment, and it can be seen that a machined, stepped profile applied in accordance with the present invention delivers reflectivity which is markedly less than other known forms of treatment.

TABLE 1

| Surface | Reflected light at isocentre Mean Lux value | Flatness maintained? | Less than 40 μm in thickness? | Radiation qualities maintained? | Adequate radiation hardness? |
| --- | --- | --- | --- | --- | --- |
| Bare leaf (untreated) | 3.5 | — | — | — | — |
| Trimite S60/1 | 0.5 | Yes | Yes | Yes | Yes |
| HS21 mist spray delivery | 0.4 | Yes | No | Yes | No |
| Matt black paint mist spray delivery | 0.6 | Yes | Yes | Yes | No |
| Etching | 2.5 | Yes | Yes | No | Yes |
| Anodising | 2.1 | Yes | Yes | Yes | Yes |
| Rough machining e.g. surface finishing wheel | 2.9 | Yes | Yes | Yes | Yes |
| Oxidised coating | 2.9 | Yes | Yes | Yes | Yes |
| Shot blasted Al | 1.6 | No | Yes | No | Yes |
| Shot blasted glass | 1.9 | No | Yes | No | Yes |
| Step profiled leaf face | 0.8 | Yes | Yes | Yes | Yes |

As can be seen, the Lux value for the machined surface is 0.8 Lux, significantly lower than is experienced using other listed methods which have been discussed earlier in this specification.

It will of course be understood that many variations may be made to the above-described embodiment without departing from the scope of the present invention.

The invention claimed is:

1. A method of treating a surface of an item for a radiotherapy apparatus, comprising the steps of machining into a planar reflective surface of the item a stepped profile comprising a plurality of steps, each step having a first surface angled to the planar reflective surface such that, in use, the first surface reflects optical light incident on the planar reflective surface away from a center of a treatment field of the radiotherapy apparatus and a second surface angled with respect to the planar reflective surface and the first surface such that, in use, the second surface is shadowed from optical light incident on the planar reflective surface by the first surface, the steps having a depth which does not exceed 2.15% of the total depth of the item.

2. The method according to claim 1 further comprising the step of assembling the item with other items to form a radiotherapeutic apparatus.

3. The method according to claim 1 in which the item is a leaf of a multi-leaf collimator.

4. The method according to claim 1 wherein the first surface is provided at an angle of between 10° and 90° to the planar surface.

5. The method according to claim 4 wherein the first surface is provided at an angle of between 30° to 60° to the planar surface.

6. The method according to claim 4 wherein the first surface is provided at an angle of 45° to the planar surface.

7. The method according to claim 1 wherein the steps are substantially identical in profile and are equally spaced across the surface.

8. The method according to claim 1 wherein the steps have a pitch of about 2 mm.

9. The method according to claim 1 wherein the steps have a depth which is less than 30 microns.

10. The method according to claim 9 wherein the depth is 20 microns or less.

11. The method according to claim 1 wherein the stepped profile is provided across substantially all of a planar reflective surface of the item.

12. The method according to claim 1 wherein the machining process is milling.

13. The method according to claim 1 wherein the machining process is selected from wire or spark eroding.

14. The method according to claim 1 wherein each step has a depth z and a pitch (x+y), a first surface D and second surface C, the first surface D being inclined to the planar surface at an angle of (90°−A) and the second surface C being inclined to the planar surface at an angle B and, in use, light is incident on the planar surface at an angle s and the relationship between A, B and s is such that $B \geq s$, $A \leq (s+45°)$ and $A \geq s$.

15. A radiotherapeutic apparatus having an interior passageway through which the radiotherapeutic apparatus is arranged to direct a beam of radiation, the radiotherapeutic apparatus comprising a part having a surface exposed to the interior passageway, at least part of that surface having been subjected to the method of claim 1.

16. A component part of a radiotherapeutic apparatus having a surface exposed to the interior passageway, at least part of that surface having been subjected to the method of claim 1.

17. The component part according to claim 16, wherein the component part comprises a leaf of a multi-leaf collimator.

* * * * *